US008273803B2

(12) United States Patent
Garigapati et al.

(10) Patent No.: US 8,273,803 B2
(45) Date of Patent: Sep. 25, 2012

(54) TETRA CALCIUM PHOSPHATE BASED ORGANOPHOSPHORUS COMPOSITIONS AND METHODS

(75) Inventors: Venkat R. Garigapati, Southborough, MA (US); Brian J. Hess, Charlestown, MA (US); Jon Ahola, Walpole, MA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 13/315,015

(22) Filed: Dec. 8, 2011

(65) Prior Publication Data
US 2012/0082705 A1  Apr. 5, 2012

Related U.S. Application Data

(62) Division of application No. 12/616,900, filed on Nov. 12, 2009, now Pat. No. 8,232,327.

(51) Int. Cl.
*A61L 24/02* (2006.01)
*C04B 12/02* (2006.01)

(52) U.S. Cl. .......................... 523/116; 523/118; 106/691

(58) Field of Classification Search .................. 523/116, 523/118; 106/691
See application file for complete search history.

(56) References Cited

U.S. PATENT DOCUMENTS

| | | | |
|---|---|---|---|
| 4,183,915 A | 1/1980 | Gaffar et al. | |
| 4,234,972 A | 11/1980 | Hench et al. | |
| 4,376,168 A | 3/1983 | Takani et al. | |
| 4,491,987 A | 1/1985 | Park | |
| 4,634,720 A | 1/1987 | Dorman et al. | |
| 4,636,526 A | 1/1987 | Dorman et al. | |
| 4,661,536 A | 4/1987 | Dorman et al. | |
| 4,672,032 A | 6/1987 | Slavkin et al. | |
| RE33,161 E | 2/1990 | Brown et al. | |
| RE33,221 E | 5/1990 | Brown et al. | |
| 5,053,212 A | 10/1991 | Constantz et al. | |
| 5,092,888 A | 3/1992 | Iwamoto et al. | |
| 5,149,368 A | 9/1992 | Liu et al. | |
| 5,338,356 A | 8/1994 | Hirano et al. | |
| 5,398,483 A | 3/1995 | Smith et al. | |
| 5,409,982 A | 4/1995 | Imura et al. | |
| 5,439,951 A | 8/1995 | Glimcher et al. | |
| 5,508,267 A * | 4/1996 | Czernuszka et al. | 424/443 |
| 5,522,893 A | 6/1996 | Chow et al. | |
| 5,525,148 A | 6/1996 | Chow et al. | |
| 5,536,575 A | 7/1996 | Imura et al. | |
| 5,542,973 A | 8/1996 | Chow et al. | |
| 5,545,254 A | 8/1996 | Chow et al. | |
| 5,626,861 A | 5/1997 | Laurencin et al. | |
| 5,691,397 A * | 11/1997 | Glimcher et al. | 523/115 |
| 5,695,729 A | 12/1997 | Chow et al. | |
| 5,766,618 A | 6/1998 | Laurencin et al. | |
| 5,782,971 A | 7/1998 | Constantz et al. | |
| 5,820,632 A | 10/1998 | Constantz et al. | |
| 5,988,171 A | 11/1999 | Sohn et al. | |
| 6,118,043 A | 9/2000 | Nies et al. | |
| 6,129,928 A | 10/2000 | Sarangapani et al. | |
| 6,287,341 B1 | 9/2001 | Lee et al. | |
| 6,325,992 B1 | 12/2001 | Chow et al. | |
| 6,331,312 B1 | 12/2001 | Lee et al. | |
| 6,335,430 B1 | 1/2002 | Qvist | |
| 6,340,648 B1 | 1/2002 | Imura et al. | |
| 6,384,196 B1 * | 5/2002 | Weis et al. | 530/356 |
| 6,395,036 B1 | 5/2002 | Czernuszka et al. | |
| 6,495,156 B2 | 12/2002 | Wenz et al. | |
| 6,533,821 B1 | 3/2003 | Lally | |
| 6,547,866 B1 | 4/2003 | Edwards et al. | |
| 6,585,992 B2 | 7/2003 | Pugh et al. | |
| 6,589,590 B2 | 7/2003 | Czernuszka et al. | |
| 6,616,742 B2 | 9/2003 | Lin et al. | |
| 6,670,293 B2 | 12/2003 | Edwards et al. | |
| 6,696,073 B2 | 2/2004 | Boyce et al. | |
| 6,793,725 B2 | 9/2004 | Chow et al. | |
| 6,808,561 B2 | 10/2004 | Genge et al. | |
| 6,808,585 B2 | 10/2004 | Boyce et al. | |
| 6,955,716 B2 | 10/2005 | Xu et al. | |
| 6,987,170 B1 | 1/2006 | Silverman et al. | |
| 7,018,460 B2 | 3/2006 | Xu et al. | |
| 7,066,999 B2 | 6/2006 | Lin et al. | |
| 7,081,161 B2 | 7/2006 | Genge et al. | |
| 7,091,260 B2 | 8/2006 | Kuehn | |
| 7,258,734 B2 | 8/2007 | Lin et al. | |
| 7,258,735 B2 | 8/2007 | Lin et al. | |
| 7,270,705 B2 | 9/2007 | Lin et al. | |
| 7,294,187 B2 | 11/2007 | Chow et al. | |
| 7,303,646 B2 | 12/2007 | Qvist | |

(Continued)

FOREIGN PATENT DOCUMENTS
WO  WO9307910  4/1993

OTHER PUBLICATIONS

International Search Report for Application No. PCT/US2009/64135 dated Apr. 2, 2010 (16 pages).
Mai et al. O-phospho-L-serine: "A Modulator of Bone Healing in Calciumphosphate Cements" Biomedizinische Technik, vol. 53, Issue 5, p. 229-233 esp. abstract, Oct. 2008 (1 page).
Ishikawa et al. "Behavior of a Calcium Phosphate Cement in Simulated Blood Plasma in Vitro" Dental Materials, vol. 10, Issue 1, pp. 26-32 esp. abstract, Jan. 1994 (1 page).
Chow et al. "A Natural Bone Cement—A Laboratory Novelty Led to the Development of Revolutionary New Biomaterials" Journal of Research of the National Institute of Standards and Technology, vol. 106, No. 6, pp. 1029-1033, Nov. 2001 (5 pages).
Fujimura et al. "A bioactive bone cement containing Bis-GMA resin and A-W glass-ceramic as an augmentation graft material on mandibular bone" Clinical Oral Implants Research, vol. 14, Issue 5, pp. 659-667 esp. abstract, Oct. 2003 (2 pages).
Bundy et al. "The Effect of Surface Preparation on Metal/Bone Cement Interfacial Strength" Journal of Biomedical Materials Research, vol. 21, Issue 6, pp. 773-805 esp. abstract, Jun. 1987 (1 page).

(Continued)

*Primary Examiner* — Tae H Yoon
(74) *Attorney, Agent, or Firm* — McCracken & Frank LLC

(57) ABSTRACT

Compositions and methods of their use to adhere a variety of materials together are disclosed herein. The compositions include at least tetra calcium phosphate, an effective amount of a compound that is structurally similar to phosphoserine, and can be mixed with an aqueous solution. The compositions provide adhesive and cohesive strength in both wet and dry environments and exhibit significant bond strength upon curing.

35 Claims, 2 Drawing Sheets

U.S. PATENT DOCUMENTS

| | | | |
|---|---|---|---|
| 7,318,841 B2 | 1/2008 | Tofighi et al. | |
| 7,407,542 B2 | 8/2008 | Lemaitre et al. | |
| 7,416,602 B2 | 8/2008 | Murphy et al. | |
| 7,473,312 B2 | 1/2009 | Barralet et al. | |
| 7,494,950 B2 | 2/2009 | Armitage et al. | |
| 7,514,248 B2 | 4/2009 | Gower et al. | |
| 7,514,249 B2 | 4/2009 | Gower et al. | |
| 7,527,687 B2 | 5/2009 | Genge et al. | |
| 7,544,496 B2 | 6/2009 | Gower et al. | |
| 7,547,449 B2 | 6/2009 | Gower et al. | |
| 7,575,628 B2 | 8/2009 | Lu et al. | |
| 7,619,016 B2 | 11/2009 | Dickens et al. | |
| 7,628,851 B2 | 12/2009 | Armitage et al. | |
| 7,632,878 B2 | 12/2009 | Xu et al. | |
| 7,648,728 B2 | 1/2010 | Yamamoto et al. | |
| 8,029,569 B2 * | 10/2011 | Aferzon et al. | 623/17.15 |
| 2001/0051815 A1 | 12/2001 | Esplin | |
| 2003/0009235 A1 | 1/2003 | Manrique et al. | |
| 2004/0002770 A1 | 1/2004 | King et al. | |
| 2005/0217538 A1 * | 10/2005 | Reinstorf et al. | 106/690 |
| 2006/0089646 A1 | 4/2006 | Bonutti | |
| 2006/0096504 A1 | 5/2006 | Grover et al. | |
| 2006/0263443 A1 | 11/2006 | Chow et al. | |
| 2007/0092580 A1 | 4/2007 | Chow et al. | |
| 2007/0092856 A1 | 4/2007 | Chow et al. | |
| 2007/0221093 A1 | 9/2007 | Erdrich et al. | |
| 2008/0009955 A1 | 1/2008 | Shimp et al. | |
| 2008/0028992 A1 | 2/2008 | Lee et al. | |
| 2008/0069852 A1 | 3/2008 | Shimp et al. | |
| 2008/0095817 A1 | 4/2008 | Murphy | |
| 2008/0188945 A1 | 8/2008 | Boyce et al. | |
| 2009/0028949 A1 | 1/2009 | Leonard et al. | |
| 2009/0028960 A1 | 1/2009 | Leonard et al. | |
| 2009/0158964 A1 | 6/2009 | Insley et al. | |
| 2009/0220475 A1 | 9/2009 | Bohner et al. | |
| 2009/0258966 A1 | 10/2009 | Hirayama et al. | |
| 2010/0120923 A1 | 5/2010 | Stewart et al. | |
| 2010/0605626 | 12/2010 | Stewart et al. | |
| 2011/0287067 A1 | 11/2011 | Stewart | |

OTHER PUBLICATIONS

Clarke "Role of Ceramic Implants, Design and Clinical Success With Total Hip Prosthetic Ceramic-to-Ceramic Bearings" Clinical Orthopaedics and Related Research, vol. 282, pp. 19-30 esp. abstract, Sep. 1992 (1 page).

International Preliminary Report on Patentability for Application No. PCT/US2009/64135 dated May 26, 2011 (14 pages).

International Search Report and Written Opinion, dated Feb. 21, 2012, International Application No. PCT/US2011/060956, Applicant Howmedica Osteonics Corp. (13 pages).

(Vo-Dinh) Nanotechnology in Biology and Medicine, CRC Press (Jan. 24, 2007) [retrieved on Feb. 8, 2012] entire document retrieved from the Internet: <URL:http://books.google.com/books/aboutNanotechnology_in_biology_and_medicine. html?id=t9lPt1Hu6bAC>, (1 page).

W. Schneiders et al., "Effect of modification of hydroxyapatite/collagen composites with sodium citrate, phosphoserine, phosphoserine/RGD-peptide and calcium carbonate on bone remodelling," Bone 40 (2007) pp. 1048-1059, Elsevier, Nov. 19, 2006, Dresden, Germany, www.elsevier.com/locate/bone (12 pages).

A. Reinstorf et al., "Phosphoserine—a convenient compound for modification of calcium phosphate bone cement collagen composites," Journal of Materials Science: Materials in Medicine 15 (2004), pp. 451-455, 2004 Kluwer Academic Publishers, Dresden, Germany (5 pages).

\* cited by examiner

TETRA CALCIUM PHOSPHATE BASED ORGANOPHOSPHORUS COMPOSITIONS AND METHODS

CROSS REFERENCE TO RELATED APPLICATIONS

The present application is a divisional of application Ser. No. 12/616,900, filed Nov. 12, 2009, and claims the benefit from the following provisional applications: Ser. No. 61/198,938, filed Nov. 12, 2008, Ser. No. 61/268,931, filed Jun. 18, 2009 and Ser. No. 61/237,762, filed Aug. 28, 2009, the disclosures of which are hereby all incorporated by reference.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

Tetra calcium phosphate based organophosphorus compositions that have significant cohesive and/or adhesive strength properties and also are physiologically-well tolerated are disclosed herein.

2. Description of the Background of the Invention

Calcium phosphate composites are used as bone substitutes and bone grafts. These calcium phosphate composites tend to form complexes primarily between calcium-based salts through charge interactions. These composites are used as general bone void fillers and generally lack the adhesive strength sufficient to adhere or fix bones together, for example, fractured surfaces. These prior compositions have insufficient chemical interaction between the calcium phosphate composite and the bone surface or other surface materials and lack sufficient strength to be used to attach bone to bone or bone to other materials.

Certain marine species, such as tubeworms and sand castle worms, rely on secreted proteins for adhesion mechanisms ("The tube cement of Phragmatopoma californica: a solid foam," Russell J. Stewart, James C. Weaver, Daniel E. Morse and J. Herbert Waite, Journal of Experimental Biology 207, 4727-4734, 2004). These adhesive proteins contain a high amount of phosphoserine relative to other amino acids. It should be noted that phosphoserine is also referred to as O-phosphoserine. This is an alternate name for the same material and in the present description we will use phosphoserine. The specific mechanism of the phosphoserine involvement with the proteins is not understood. However, phosphoserine has been reported by Reinstorf et al. to be responsible for a specific interaction with calcium containing hydroxyapatite (HA) of bone in U.S. Patent Application Publication No. 2005-0217538A1. In this publication, the authors describe calcium phosphate cements, which do not contain tetra calcium based compositions, modified with phosphoserine in an amount from 0.5% to 5% weight of the composition. The phosphoserine is described as aiding compressive strength and is used as a surface area modifier in the bone cement material. When phosphoserine is used in the range from 0.5% to 5% weight of the composition, the resulting compositions do not exhibit appreciable bone adhesion properties.

SUMMARY OF THE INVENTION

One embodiment of the present invention is a composition that comprises a mixture of tetra calcium phosphate; and a compound of the formula

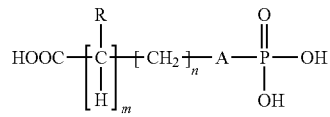

where A is O, $CH_2$, or S; R is H, $NH_2$, $NHCO(CH_2)_t CH_3$ where t is 0 to 2, $NH(CH_2)_x CH_3$ where x is 0 to 3, $NR1R2$ where R1 is $(CH_2)_y CH_3$ and R2 is $(CH_2)_y CH_3$ where y is 0 to 2, $(CH_2)_z CH_3$ where z is 0 to 3, where m is 0 to 1, and where n is 0 to 3 and wherein the compound is present in an amount from about 10% by weight based on the combined weight of the tetra calcium phosphate and the compound, and an aqueous medium.

A further embodiment of the present invention comprises a method of repairing a hard surface comprising the steps of mixing a composition comprising an effective amount of tetra calcium phosphate and a compound of the formula

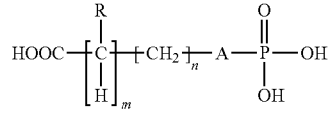

where A is O, $CH_2$, or S; R is H, $NH_2$, $NHCO(CH_2)_t CH_3$ where t is 0 to 2, $NH(CH_2)_x CH_3$ where x is 0 to 3, $NR1R2$ where R1 is $(CH_2)_y CH_3$ and R2 is $(CH_2)_y CH_3$ where y is 0 to 2, $(CH_2)_z CH_3$ where z is 0 to 3, where m is 0 to 1, and where n is 0 to 3 and wherein the compound is present in an amount from about 10% by weight based on the combined weight of the tetra calcium phosphate and the compound, with sufficient aqueous medium to create a mixture; applying the mixture to the hard surface to be repaired; and allowing the mixture to cure.

A still further embodiment of the present invention is a composition that comprises a mixture of tetra calcium phosphate; and a compound of the formula;

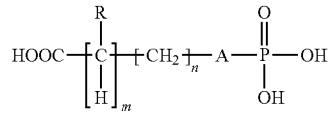

where A is O, $CH_2$, or S; R is H, $NH_2$, $NHCO(CH_2)_t CH_3$ where t is 0 to 2, $NH(CH_2)_x CH_3$ where x is 0 to 3, $NR1R2$ where R1 is $(CH_2)_y CH_3$ and R2 is $(CH_2)_y CH_3$ where y is 0 to 2, $(CH_2)_z CH_3$ where z is 0 to 3, where m is 0 to 1, and where n is 0 to 3 and wherein the compound is present in an amount from about 10% by weight based on the combined weight of the tetra calcium phosphate and the compound.

Yet another embodiment of the present invention is a kit for forming calcium phosphate bone restorative product that comprises a composition comprising an effective amount of tetra calcium phosphate and a compound of the formula

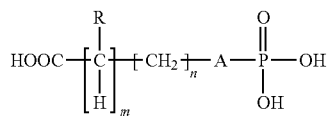

where A is O, $CH_2$, or S; R is H, $NH_2$, $NHCO(CH_2)_tCH_3$ where t is 0 to 2, $NH(CH_2)_xCH_3$ where x is 0 to 3, NR1R2 where R1 is $(CH_2)_yCH_3$ and R2 is $(CH_2)_yCH_3$ where y is 0 to 2, $(CH_2)_zCH_3$ where z is 0 to 3, where m is 0 to 1, and where n is 0 to 3 and wherein the compound is present in an amount from about 10% by weight based on the combined weight of the tetra calcium phosphate and the compound contained within a first container; and an aqueous medium contained within a second container.

An additional embodiment of the present invention comprises a method of repairing a bone structure that comprises the steps of applying a composition comprising an effective amount of tetra calcium phosphate and a compound of the formula

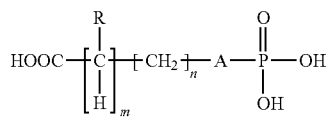

where A is O, $CH_2$, or S; R is H, $NH_2$, $NHCO(CH_2)_tCH_3$ where t is 0 to 2, $NH(CH_2)_xCH_3$ where x is 0 to 3, NR1R2 where R1 is $(CH_2)_yCH_3$ and R2 is $(CH_2)_yCH_3$ where y is 0 to 2, $(CH_2)_zCH_3$ where z is 0 to 3, where m is 0 to 1, and where n is 0 to 3 and wherein the compound is present in an amount from about 10% by weight based on the combined weight of the tetra calcium phosphate and the compound directly to the bone structure to be repaired; and allowing the composition to harden by combining in situ with aqueous based bodily fluids.

A still further embodiment of the present invention is a composition that comprises an effective amount of tetra calcium phosphate, a compound of the formula

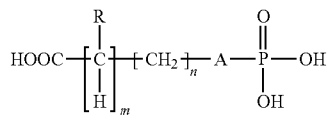

where A is O, $CH_2$, or S; R is H, $NH_2$, $NHCO(CH_2)_tCH_3$ where t is 0 to 2, $NH(CH_2)_xCH_3$ where x is 0 to 3, NR1R2 where R1 is $(CH_2)_yCH_3$ and R2 is $(CH_2)_yCH_3$ where y is 0 to 2, $(CH_2)_zCH_3$ where z is 0 to 3, where m is 0 to 1, and where n is 0 to 3 and an aqueous medium wherein the composition has a tacky state for up to about 12 minutes after the composition is mixed with the aqueous medium, has a separation strength in the range of about 10 kPa to about 150 kPa during the tacky state, has a putty state for up to about 15 minutes after the composition is mixed with the aqueous medium, and an adhesive strength upon curing of greater than 250 kPa.

An additional embodiment of the present invention comprises a method of joining bone to an other material comprising the steps of mixing a composition comprising an effective amount of tetra calcium phosphate and a compound of the formula

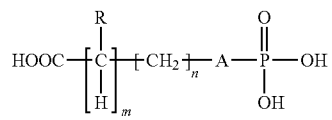

where A is O, $CH_2$, or S; R is H, $NH_2$, $NHCO(CH_2)_tCH_3$ where t is 0 to 2, $NH(CH_2)_xCH_3$ where x is 0 to 3, NR1R2 where R1 is $(CH_2)_yCH_3$ and R2 is $(CH_2)_yCH_3$ where y is 0 to 2, $(CH_2)_zCH_3$ where z is 0 to 3, where m is 0 to 1, and where n is 0 to 3 and wherein the compound is present in an amount from about 10% by weight based on the combined weight of the tetra calcium phosphate and the compound, with sufficient aqueous medium to create a mixture and applying the mixture to a surface of the bone. The method further includes the steps of placing the surface of the bone into contact with a material to be joined to the bone; and allowing the mixture to cure.

Other aspects and advantages of the present invention will become apparent upon consideration of the following detailed description.

DETAILED DESCRIPTION OF THE PREFERRED EMBODIMENTS

Figure 1:
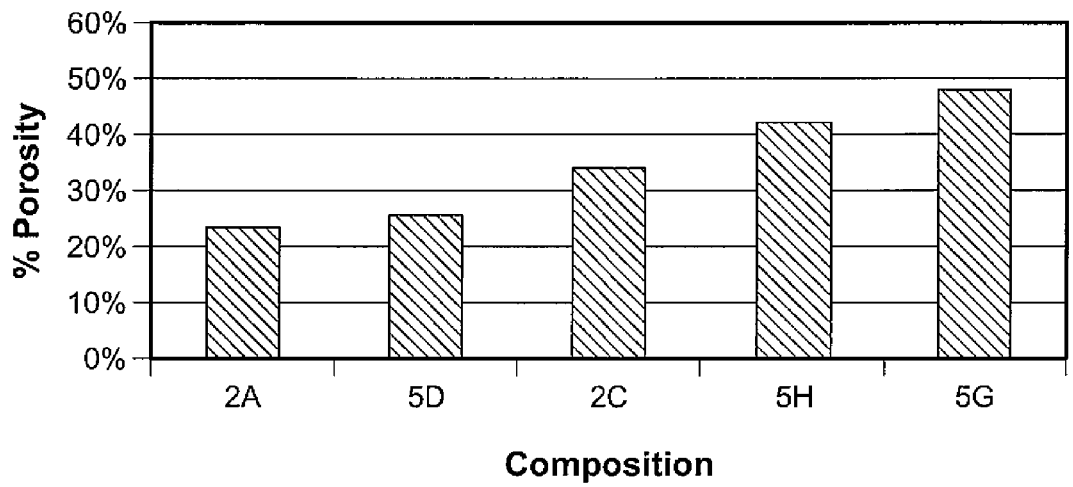
FIG. 1 a graph of percentage porosity of selected compositions.

The compositions as described herein have many unique properties not found in prior calcium phosphate compositions. One particularly important property is that the compositions have a tacky state immediately subsequent to mixing with an aqueous medium. This tacky property is retained for a number of minutes, sometimes up to 12 minutes depending on the application requirement, typically up to about 4 minutes, and preferably up to about 2 minutes, after mixing with the aqueous medium. The time of the tacky state is dependent on a number of factors including relative ratio of the components, the particle sizes of the component materials, the presence of additives and the like. During this time the compositions will adhere bone to bone and bone to other materials, often without the need for external clamping or other application of pressure. The tacky state is not so aggressive that the composition will permanently affix the materials together at this point in time. Rather the tacky state can allow the materials to be moved relative to each other and also to be re-opposed without appreciable loss of ultimate cured strength. This is important in a medical setting so that the user can make sure the bone and the other material to be adhered to the bone are in the proper position relative to each other.

The tacky state is followed by a putty state. In the putty state, the tacky property has substantially disappeared and the compositions can be shaped or sculpted. In addition, during the putty state, the composition can be formed into shapes or used to fill voids in bone in a manner similar to putty. This putty state is retained for a number of minutes, sometimes up to 15 minutes depending on the application requirement, typically up to about 8 minutes, and preferably up to about 5 minutes, after mixing with the aqueous medium. Like the tacky states, the putty state is dependant on a number of factors including the relative ratio of the components, the presence of additives, the particle size of the components and the like. Because the items to be affixed can be repositioned during the tacky state or the compositions can be shaped during the putty state, this combined time of the tacky state and the putty state is some times referred to as the working time. Typical compositions have a working time of up to 8 minutes from initial mixing and often the working time is up to about 5 minutes after which time the compositions have sufficiently begun hardening that further manipulation will result in degradation of ultimate strength of the bond.

After the putty state, the compositions harden like a cement to form a substantially permanent bond between the materials. In the cement state, the composition hardens and the materials that have been affixed to each other cannot be separated without the application of significant force. The compositions typically will begin to harden within about 8 minutes, and often within about 5 minutes, after mixing with the aqueous medium. The amount of time to reach the cement state is also dependant of the same factors listed above.

A further important property of the compositions is that these compositions have significant coherency and integrity within a wet environment. In the medical field, this would include a surgical site, a wound or similar situation where blood and other bodily fluids are present. The tacky state, the putty state and the cement state all occur in either a wet environment or in a dry environment. In order to get the desirable properties, the user need not ensure that the application site is clean and dry. In a wet environment, the compositions tend to remain together and the presence of the liquid does not significantly affect the integrity of the composition or the ultimate strength properties.

The compositions as described herein are useful in a wide variety of medical applications. One use of the compositions is to adhere bone fragments together within the body. This is useful, for example, during surgery to allow for temporary fixation prior to definitive hardware placement, and to enhance fracture fixation by adhering both load and non-load bone fragments together alone or in the presence of appropriate immobilization. The compositions also enhance screw or bone anchor fixation into low density cancellous bone at and/or after surgery, to allow screw fixation when the core diameter of the screw hole is larger then the screw major diameter, for instance to reattach screws that have stripped from the surrounding material, to adhere a metal or bioresorbable plate to fractured bones allowing for reduction and/or elimination of metal or bioresorbable screws used to fix plate to bone. The compositions also have the capacity to enhance fixation of a joint replacement prosthesis to bone (e.g. hip acetabular cup or femoral stem). The compositions adhere the junction of at least one of a tendon, ligament, cartilage, a bone graft, and/or dental implants to bone. The compositions may be used to support new bone growth for dental socket or dental ridge augmentation. The compositions have the capacity to adhere to bony defect perimeters while filling gaps creating a seal to prevent leakage (e.g. cerebral spinal fluid). Furthermore, the compositions may also be used in ossicular chain reconstruction to adhere middle ear ossicles together. The adhesive properties of the compositions of the present invention to bone and bone to other materials make them useful to provide bony contour for facial bone augmentation applications. These compositions are also useful for gluing cancellous bones, cortical bones and a combination of both, whether in fatty or greasy environments potentially without any surface pretreatment prior to application.

One particularly useful use of the compositions is as a bone restorative composition. By a bone restorative composition is meant a composition that is useful to restore and/or repair bone, such as bone adhesives, bone cements, bone glues, bone putties, bone void fillers, bone replacement compositions, cements and/or adhesives to fix screws, implants and at least one of a tendon, ligament, cartilage, a bone graft, and/or a dental implants to bone.

As noted above, the compositions have a tacky state shortly after initial mixing. This tacky state enables two items, such as two pieces of bone, bone and another material or two non-bone materials to be held together by the composition itself, without the need for external force, until the composition sets to the final hardened cement state. The amount of force needed to remove two opposed pieces of material from each other is the separation strength. For the composition as described herein, these compositions have a separation strength during the tacky state within the first 4 minutes and preferably within the first 2 minutes after initial mixing from about 10 kPa to about 250 kPa and preferably from about 50 kPa to about 150 kPa. For certain applications it may be useful to have a longer tacky state whereby certain compositions have a separation strength which continues in this range for up to 12 minutes. This separation strength is sufficiently high that the items to be joined need not be held together unless there is an apposing strength of the items greater than the separation strength and also, the items can still be repositioned or even reapposed without loss of ultimate bond strength.

It has been found that in the present compositions tetra calcium phosphate (TTCP) has unusual properties not shared by other calcium phosphate compositions. TTCP is the most basic of all the calcium phosphates; therefore, it readily reacts to acidic compounds. While other calcium phosphate compositions can be used in addition to the TTCP, the compositions must include an effective amount of TTCP. The TTCP used in the present compositions can be made by a variety of methods. One such manufacturing method is disclosed by Chow and Takagi in U.S. Pat. No. 6,325,992, the disclosure of which is hereby incorporated by reference. The TTCP can be 100% pure material or can include other calcium and calcium phosphate materials as an impurity, e.g. α-TCP, CaO and/or HA.

A second necessary component of the compositions is a compound that has the following formula;

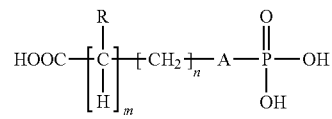

where A is O, $CH_2$, or S; R is H, $NH_2$, $NHCO(CH_2)_tCH_3$ where t is 0 to 2, $NH(CH_2)_zCH_3$ where x is 0 to 3, NR1R2 where R1 is $(CH_2)_yCH_3$ and R2 is $(CH_2)_yCH_3$ where y is 0 to 2, $(CH_2)_zCH_3$ where z is 0 to 3, where m is 0 to 1, and where n is 0 to 3. Preferred compounds are those where A is O or $CH_2$, R is H or $NH_2$, m is 0 or 1 and n is 0 or 1. The most preferred compound is phosphoserine that has the following structure;

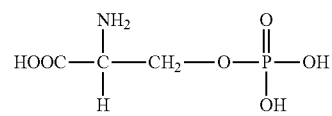

The compounds that are structurally similar to phosphoserine, which contain the reactive phosphonate or phosphate, and which have COOH functional groups, are capable of interacting with the Ca$^+$ within the TTCP to form a calcium based matrix and are referred to as compounds structurally similar to phosphoserine in this description. The combination of these functional groups plus the geometry such as the chain length between the phosphorous and the COOH are unique aspects to the molecules which affect the level of adhesive bonding strength to substrate surfaces such as bone and metal.

The preferred compound that is structurally similar to phosphoserine is phosphoserine which may be any form of phosphoserine, including the phospho-D-serine, phospho-L-serine or the phospho-DL-serine forms may be used. The stereochemistry of the phosphoserine does not seem to have any impact on the properties of the compositions disclosed herein.

It has been found that when the quantity of compounds that are structurally similar to phosphoserine is increased beyond about 10% w/w of the combination of the compound and the TTCP, more generally in the range of about 10% to about 90%, more typically in the range of 15% to about 50%, or preferably from about 20% to about 40%, the tacky and adhesion properties of the resulting compositions were significant. At such levels, the influence of compounds that are structurally similar to phosphoserine extends beyond internal interaction with the cement, but also extends to significant binding with the hydroxyapatite architecture and proteins of bone. At below about 10% by weight of the compound structurally similar to phosphoserine, the compositions do not have a tacky state and these compositions do not have adhesive properties.

Factors that may affect the length of the tacky state, the length of the putty states and the ultimate cure time, as well as strength properties of the compositions include: the percentage (w/w) TTCP and the compounds that are structurally similar to phosphoserine based solely on the weight of the TTCP and the compounds that are structurally similar to phosphoserine in the composition, the selection of the compounds that are structurally similar to phosphoserine, the particle size of the TTCP, and the nature and quantity of any additives and/or fillers which may be combined to the composition to enhance the material properties.

The mean particle size of the TTCP should be below 1000 μm, preferably 1-250 μm, most preferably 10-100 μm. As the mean particle size of the TTCP is reduced, the TTCP tends to dissolve too fast and these compositions may not be practical for all uses as disclosed herein. On the other hand if the TTCP has a mean particle size of greater than about 1000 μm, the intra-operative performance of the compositions may not have the desired initial strength and be too slow to set. If a longer working time is desired, then TTCP with a larger mean particle size can be used; however, if a shorter working time is desired, then TTCP with a smaller mean particle sizes can be used. In certain use environments, compositions that have a multi-modal mean particle size distribution with, for example, one mode less then 50 μm and the other mode above 50 μm can provide unique properties such as a fast initial cure rate from the smaller mean particle size mode combined with higher intrinsic compression strength of the material from the larger mean particle size mode.

The aqueous based mixing media useful for combining the TTCP and compound that is structurally similar to phosphoserine powders can include water, buffers such as sodium phosphate, saline, and blood based products such as whole blood, plasma, platelet rich plasma, serum, and/or bone marrow aspirate. The blood based products are used with the goal of achieving enhanced rate of bone healing and remodeling. It is also possible to use the compositions without premixing with an aqueous medium if the composition is to be used in a sufficiently wet environment that the aqueous medium can be absorbed from the in situ site. In this situation, the composition can be dusted on or otherwise applied to the desired site and then mixed with the liquids that are already present at the site.

Additives may enhance the material properties. These properties include the handling, porosity, intrinsic material strength, & bone healing rate (osteogenic). Suitable additives include: alpha or beta tri-calcium phosphate (α-TCP or β-TCP), calcium sulfate, calcium silicate, calcium carbonate, sodium bicarbonate, sodium chloride, potassium chloride glycerol phosphate disodium, amino acids such as serine, excess amounts of phosphoserine, polyols (such as glycerol, mannitol, sorbitol, trehalose, lactose, & sucrose), silk, keratin (primarily found in human hair), autologous bone powder or chips, demineralized bone powder or chips, collagen, various biodegradable polymers such as poly ethylene glycol (PEG), poly lactic acid (PLLA), poly glycolic acid (PGA), and copolymers of lactic and glycolic acid (PLGA), further including biodegradable block polymers such as poly lactic acid (PLLA)-polyethylene glycol (PEG)-poly lactic acid (PLLA) block polymer, BMP7, stem cells, parathyroid hormone (PTH), bisphosphonates, and mixtures thereof. In addition, other additives and/or fillers could be incorporated which offer surgical visual aids & anti-infective properties.

The α-TCP and β-TCP additive component typically is also in granular form. The granules presently contemplated have an overall diameter size in the range of about 0.1 to 2 mm, or preferably between 0.5 to about 1 mm. Larger and smaller granules can be used depending on the other components of the composition and the desired end properties. In the present compositions, the particle size of the granules has an impact on the mechanical strengths of the resultant compositions. The total porosity of these granules is in the range of 40-80%, more preferably 65-75%, and the average pore diameter size of the granules in these compositions is in the range of 20-500 μm, preferably 50-125 μm. The granules do not dissolve within the present embodiments during the curing phase, but interacts as a solid particle with the other components of the compositions. In the present compositions, the porosity and pore size listed here has an impact on the resorption characteristics of the resultant compositions and to allow for bony in growth and healing as described by Dalal et al. in U.S. Pat. No. 6,949,251.

The additives that affect the porosity include cement curing pore forming agents such as calcium carbonate or sodium bicarbonate, granules with pre-formed pores made from alpha or beta tri-calcium phosphate (α-TCP or β-TCP), biodegradable polymers usually in fiber form that open channels or pores as they degrade relatively quick in vivo such as PGA, or copolymers such as PLGA, or biodegradable fibers that open channels or pores as they degrade over relatively long time periods such as PLLA, silk, keratin, collagen, autologous bone powder or chips, or demineralized bone powder or chips. Other biodegradable polymers not in the form of fibers, rather powders, can be used such as PLLA, PGA, PLGA, PEG, or block polymers such as PLLA-PEG-PLLA. Small molecules may also be used which leach away relatively quickly from the cement as it cures; these materials may include sodium chloride, potassium chloride, glycerol phosphate disodium, polyols (such as glycerol, mannitol, sorbitol, trehalose, lactose, & sucrose), amino acids such as serine, and/or excess amounts of phosphoserine. Other materials that form pores may dissolve or resorb over time in vivo and release from the cement opening pores; these materials include calcium sulfate, α-TCP or β-TCP powder or granules. Granules can be used to alter the in vivo resorption profile, such as α-TCP or β-TCP granules, or hybrid granules made from calcium sulfate and α-TCP or β-TCP in which the calcium sulfate portion resorbs more quickly.

The additives that affect the bone healing rate driven by new bone ingrowth can be influenced by the level of porosity of the cured cement. This rate can be manipulated by the number of pores and size of the pores created within the cured cement. Achieving such porosity up to 60% v/v was demonstrated by controlling the ratio of composition ingredients. The porosity that develops during the curing process can be controlled by the amount of pore forming agent added (such as calcium carbonate), the level of compound structurally similar to phosphoserine added, the level of aqueous solution used, and/or the level of other agents added to the composition. Increasing the porosity reduces the material intrinsic strength; however, a balance of porosity vs. strength is critical for achieving the clinical application. Additives that increase the intrinsic material strength can be incorporated to offset the loss of strength by creating porosity.

The additives that increase the intrinsic material strength of the cured cement include silk, keratin, collagen, autologous bone powder or chips, demineralized bone powder or chips, calcium silicate, calcium sulfate, biodegradable polymers (such as PLLA, PGA, PLGA) or biodegradable block polymers (such as PLLA-PEG-PLLA), also granules made from calcium sulphate, α-TCP, β-TCP or hybrids thereof. These material additives improve the intrinsic strength or toughness by preventing crack propagation in the cement when under load. These material additives can be supplied as granules, powders or fibers. An important aspect of these fibers is the size. The size can be defined by the aspect ratio (length: diameter). The preferred aspect ratio is from 2:1 to 50:1; more preferable from 10:1 to 30:1. The overall length of the fiber can be up to 5 mm; however, since the material could be used as bone to bone adhesive, the length of the fiber may be more appropriate at lengths up to 2 mm. The additives can be added into the composition up to 30% w/w based on the total weight of the composition to increase the intrinsic strength of the material; however, as such levels the adhesive properties decrease; therefore, a balance between intrinsic strength and material adhesive properties is required.

The additives that act as visual aids in the surgical procedure include colorants such as a pigment or dye to aid in determining coverage and depth of the applied cement or contrast agents such as barium salts in determining depth on a radiograph.

Other additives can be incorporated into the compositions that enhance the bone healing rate (osteogenic) These additives comprise a class of osteogenic growth factors including bone morphogenetic proteins (BMP's), such as BMP 7, stem cells, parathyroid hormone (PTH) and/or anti-osteoporotic agents such as bisphosphonates can be contemplated for incorporation into the composition.

Other additives that can be incorporated into the composition are infection preventatives such as broad spectrum antibiotics and anti-infectic additives.

While not wishing to be bound by theory, compositions of the present disclosure are believed to function as follows: the TTCP, which is basic in nature, reacts with the compound that is structurally similar to phosphoserine, which is acidic in nature, upon mixing with the aqueous medium and forms a hardened, layered structure upon curing. This reaction is exothermic; the degree of exothermic activity depends on a number of factors including the volume of the composition. The low pH nature of the compounds that are structurally similar to phosphoserine enable the hydroxyl of phosphate or phosphonate and COOH functional group to bond through ionic interaction with the calcium ions from within the TTCP. This resulting reactive intermediate continues a cascade of ionic interactions with calcium and phosphate ions within the TTCP or HA on the bone surface or any other metal ions of the metal implants. This series of interactions provides transient material having the tacky properties while curing and the adhesion strength that increases upon cure.

The exothermic properties of the composition when curing are prevalent when mixing as a large volume bone void filler (usually greater then 10 cc) and this may serve as an effective means to kill the residual tumor cells locally that remain after surgical bone tumor removal.

The exothermic properties of the composition may lead to necrosis of local tissue and this also reduces the adhesive working time. The amount of heat released by the exothermic reaction is mainly influenced by the volume of the composition, the size of the particles and the ratio of compound that is structurally similar to phosphoserine to TTCP. With larger volumes of composition, more heat is released to the surrounding tissue. With volumes less than or equal to 1 cc, the heat release is negligible with maximum temperature reached during the curing of the adhesive being below 40° C. The higher volume compositions greater than 1 cc, led to considerable heat release, even exceeding 60° C. in compositions greater than 5 cc. To manage this exothermic heat release to below 45° C., the particle size distribution of the TTCP, and the ratio of TTCP to compound that is structurally similar to phosphoserine can be chosen appropriately. The smaller TTCP particles dissolve and react faster due to a higher specific surface area; therefore, to reduce the exothermic heat release, the composition can be adjusted by choosing a TTCP particle size distribution which generally has a mean particle size greater than 15 μm, more specifically 25 μm. In addition, the greater the amount of TTCP to the compound that is structurally similar to phosphoserine used, results in a faster reaction due to the number of calcium ions available for bonding. Exothermic heat release can be limited by adding more compound that is structurally similar to phosphoserine to the composition. To further reduce the exothermic heat release, endothermic additives can be incorporated into the composition to slow the reaction rate; these include polyols (such as sorbitol or mannitol) or PEG. The factors discussed here can be chosen to design several compositions; all of which have exothermic profiles which limit or eliminate necrotic reactions to local tissues while tailoring the compositions with sufficient working time for the clinical application.

The compositions when mixed with aqueous medium typically have a creamy or a tacky paste consistency initially. Also, the mixing of the compositions with the aqueous medium does not require a high level of force or shear and simple hand mixing, such as with a spatula, is sufficient in most instances. It is envisioned that the present compositions may be applied via injection through a syringe or other suitable pressurized implement, applied with a spatula, and as otherwise desirable by a user. The creamy or tacky viscosity allows for application of the composition to the defect site for a defined period of time. The compositions allow the bone to be repositioned several times within 4 minutes and preferably within 2 minutes without losing tacky properties. If the compositions need to be injected through a syringe or cannula, the viscosity of the composition during the working time can be important. For these situations, viscosities of the compositions herein should be preferably below about 150 centipoise.

Still further embodiments have a consistency similar to putty. These embodiments are useful for filling larger defects, have sculpting properties, or for mechanical interlocking into cancellous bone. These compositions hold their cohesive, tacky, and sculpting properties over a longer period of time even when subjected to a wet field. The compositions have working time for sculpting sometimes up to 15 minutes depending on the application requirement, typically up to about 8 minutes, and preferably up to about 5 minutes, after mixing with the aqueous medium. Formulations with an increased amount of compound that is structurally similar to phosphoserine greater than 25% w/w or increased TTCP mean particle size greater than about 250 microns tend to have longer working times and seem to be suitable for use in situations were the putty will fill defects in structures that are well supported by surrounding bone. In these situations the putty does not need to harden as fast provided it maintains its cohesive properties in the wet field. Another property of the compositions is that the compositions will adhere to themselves as well as to an external surface such as bone. This is useful in situations where a shape is formed during the putty state and this shape can then adhere to bone. Also, in some instances a user may apply a mass of the composition to a bone or other surface and then shape the composition into the final desired shape during the working time of the composition.

Compositions which have a putty consistency to be used a void filler can be enhanced by incorporating macro porous granules or chips to allow for new bone ingrowth. These granules may come from synthetic sources such α-TCP or β-TCP granules or it may be preferred to select the granules or chips from autologous bone sources or demineralized bone to enhance the bone healing rate.

It is further envisioned that the cement compositions disclosed herein may be packaged into kits that may include a vial containing the TTCP with the compound that is structurally similar to phosphoserine pre-filled together and packaged under vacuum, nitrogen, or dry air to preserve the shelf life. Further, if additives are used, they may be included within this vial or in a separate vial. The aqueous medium is provided in a separate vial. The kit may include mixing bowls, stirring sticks, spatulas, syringes, and/or any other desirable component for application.

Composition of the current disclosure are envisioned to provide ease of use in different medical applications based on ease of application, duration of use before cure, resistance to in vivo environments, extended maneuverability of bone fragments and/or implant devices prior to cure onset, good load bearing capabilities after cure, and good ultimate bond strength. For example, compositions may have an adequate working period after mixing sometimes up to 15 minutes depending on the application requirement, typically up to about 8 minutes or less, and preferably up to about 5 minutes or less. Further, the relative force of pressure required to inject the composition from an appropriately sized syringe may remain constant or below a certain injection force threshold from the point of mixing and loading the syringe to the end of the working period. It is contemplated that bone fragments adhered together or implanted devices may exhibit moderate separation strengths within the working period. Such moderate separation strengths may be exhibited regardless of the relative compressive force used during apposition. It is further contemplated that cement compositions of the present disclosure may have sufficient material cohesion when applied in moist, wet, greasy and/or fatty saline environments, such as in vivo settings, thereby reducing the need for surface preparation and maintaining a dry environment. As well, good capacity for supporting passive movement and maintaining load and non-load bearing bone fragment alignment after surgery during initial rehabilitation period and active range of motion rehabilitation period are envisioned for cement compositions contemplated herein.

Typical compositions exhibit an adhesive strength upon curing, typically after greater than 10 minutes from initial mixing, in the range of about 250 to about 2000 kPa on cancellous bone and from about 250 to about 10,000 kPa on cortical bone in at least one of compression, tension, shear, and/or bending. Compositions can be chosen to achieve the strength in these ranges; the level of strength required is dependent upon the clinical application. Also it is important to note that the curing can be either in a wet environment, such as in bodily fluids, or in a dry environment, and the ultimate strength of the bond after cure does not seem to be significantly affected.

In the following examples all shear, tension and bending testing was done using an Instron Force test machine setup as follows. For shear testing the sample was supported and fastened to the machine at one end of the sample and the other end was left free and unsupported. For shear testing the samples have a bond surface that was 90° to the face of the bone samples unless there was an indication that the bond surface was at an angle of 45° from the face of the bone surface. The force test probe was placed in plane against the top of the bond line of the sample and force was applied until failure. For tension testing each end of the sample was clamped to the testing machine and the force was applied at 90° to the bond to pull the sample apart. When the bond fails the result was recorded. For the 3 point bending testing each end of the sample was supported without clamping the sample to create a span distance of 35 mm. Force was applied by the force probe to the top of the sample at the center point (same position as the bond line) between both ends until the bond fails. The TTCP that was used in all the following examples was a commercially available material that included from about 17% to 32% of related impurities. These materials all contained about 68% to 83% TTCP.

EXAMPLE 1

Each composition in Table 1 was mixed for 20 seconds in a polycarbonate bowl using either a polycarbonate pestle or spatula. After mixing, the composition was applied to both surfaces of bovine cortical bone cubes that had apposing faces using a spatula. The faces were created with either a 45° angle for the 45° shear/tension test (10×14 mm face) or a 90° angle for isolated shear, tension, or bending tests (9×9.5 mm face). Prior to testing, the bone cubes were incubated within a phosphate buffered saline (PBS) solution bath at 30° C. and had pre-dampened surfaces during composition application. By 90 seconds from the start of mixing, the apposing faces were adhered together and aligned with minimal hand compression force for 10 seconds and were immediately transferred and submerged within a PBS solution bath held at 30° C. for the duration of the cure time. If cured for longer then 10 min, the cubes were incubated at 37° C. After the cure time indicated, the cubes were loaded onto the sample fixtures and tested on an Instron force test machine. In the table, n=# is the number of replicates.

TABLE 1

| Composition | 1A | 1B | 1C |
|---|---|---|---|
| TTCP | 400 mg | 400 mg | 400 mg |
| Phosphoserine | 185 mg | 150 mg | 250 mg |
| Water | 130 μl | 130 μl | 135 μl |
| Adhesive Strength (kPa), Cure = 5 min | 1520 (n = 1) (45° Shear/Tension) | 3300 (n = 4) (Shear) | 2290 (n = 3) (Shear) |

EXAMPLE 2

The compositions of Table 2 were prepared and tested in the same manner as in Example 1. All testing was on cortical bovine bone unless otherwise indicated as cancellous bovine bone. All testing was conducted at 5 minutes cure unless otherwise indicated. All testing was 90° shear testing unless otherwise indicated.

TABLE 2

| Composition | 2A | 2B | 2C | 2D | 2E |
|---|---|---|---|---|---|
| TTCP | 400 mg | 400 mg | 400 mg | 400 mg | 400 mg |
| Phosphoserine | 185 mg | 250 mg | 267 mg | 185 mg | 280 mg |
| β-TCP granules | 100 mg | 133 mg | 133 mg | 100 mg | 400 mg |
| Water | 130 μl | 175 μl | 146 μl | | |
| Blood, fetal bovine | | | | 130 μl | |
| 20% PEG solution, Mol. Wt. = 3350, | | | | | 220 μl |
| Adhesive Strength (kPa) | 2690 (n = 6); 2340 (n = 6) (Tension); 6260 (n = 6) (3 Pt bending); 1020 (n = 6) cancellous; 450 (n = 6) cancellous (Tension); 860 (n = 6) cancellous (3 Pt bending) | 1300 (n = 1); 2130 (n = 1) @ 10 min cure | 1620 (n = 1); 2360 (n = 1) @ 10 min cure | 2560 (n = 3) | Not tacky to surgical gloves during working period |

EXAMPLE 3

The compositions of Table 3 were prepared and tested in the same manner as in Example 1. All testing was on cortical bovine bone. All testing was conducted at 5 minutes cure. All testing was 45° Shear/Tension.

TABLE 3

| Composition | 3A | 3B | 3C | 3D |
|---|---|---|---|---|
| TTCP | 400 mg | 400 mg | 400 mg | 400 mg |
| Phosphoserine | 185 mg | 185 mg | 185 mg | 185 mg |
| Water | 130 μl | 130 μl | 130 μl | 130 μl |
| α-TCP granules | 100 mg | | | |
| Calcium sulfate powder | | 100 mg | 50 mg | 100 mg |
| β-TCP granules | | | 100 mg | 50 mg |
| Adhesive Strength (kPa) | 2609 (n = 3) | 2321 (n = 1) | 2671 (n = 1) | 2314 (n = 1) |

EXAMPLE 4

The compositions of Table 4 were prepared and tested in the same manner as in Example 1. All testing was on cortical bovine bone. All testing was conducted at 5 minutes cure. All testing was 45° Shear/Tension.

TABLE 4

| Composition | 4A | 4B | 4C |
|---|---|---|---|
| TTCP | 400 mg | 400 mg | 400 mg |
| Phosphoserine | 185 mg | | |
| Carboxy ethyl phosphonate | | 185 mg | |
| Phosphonoacetic acid | | | 185 mg |
| β-TCP granules | 100 mg | 100 mg | 100 mg |
| Water | 130 μl | 130 μl | 150 μl |
| Adhesive Strength (kPa) | 2500 (n = 1) | 653 (n = 1) | 549 (n = 1) |

EXAMPLE 5

The compositions of Table 5A were prepared and tested in the same manner as in Example 1. The results of all testing are shown in Table 5B. All testing was on cortical bovine bone unless otherwise indicated. All testing was conducted at 5 minutes cure unless otherwise indicated. All testing was 45° Shear/Tension unless otherwise indicated.

TABLE 5A

| Composition | 5A | 5B | 5C | 5D | 5E | 5F | 5G | 5H |
|---|---|---|---|---|---|---|---|---|
| TTCP, mg | 400 | 400 | 400 | 400 | 400 | 400 | 400 | 400 |
| Phosphoserine, mg | 185 | 185 | 185 | 185 | 185 | 185 | 185 | 185 |
| Water, μl | 130 | 130 | 130 | 130 | 130 | 130 | 130 | 130 |
| β-TCP granules, mg | 100 | 100 | 100 | 100 | 100 | 100 | 100 | 100 |
| Calcium carbonate powder, mg | 100 | 50 | 35 | 27 | 21 | 20 | 14 | 7 |

TABLE 5B

| Example | Adhesive Strength (kPa) |
|---|---|
| 5A | 825 (n = 2); 190 (n = 2), cancellous |
| 5B | 1496 (n = 2) 423 (n = 3), cancellous |
| 5C | No strength data |
| 5D | 320 (n = 1) (Shear) 720 (n = 1) @ 10 min cure (Shear) |
| 5E | 300 (n = 1) (Shear) 750 (n = 1) @ 10 min cure (Shear) |
| 5F | 1830 (n = 6) (Shear) 1390 (n = 6) (Tension) 3930 (n = 6) (3 Pt Bending) 660 (n = 6), cancellous (Shear) 660 (n = 6), cancellous (3 Pt bending) |
| 5G | 410 (n = 1) (Shear) 800 (n = 1) @ 10 min cure (Shear) 745 (n = 2) (3 Pt bending) |
| 5H | 1500 (n = 1) @ 10 min cure (Shear) |

EXAMPLE 6

Compositions with enhanced bony in-growth properties are important for clinical use. This can be achieved by enhancing the porosity of the compositions. Certain compositions listed in FIG. 1 were prepared and tested in the same manner as in Example 1 and formed into thin disks. Each disc was 10 mm in diameter and 2 mm in height. Each sample was allowed to cure at 37° C. for 24 hrs submerged in PBS solution. After curing, the sample was dried over night in a desiccator. The sample porosity was analyzed by Mercury Intrusion Porosimetry. The results of all testing is shown in FIG. 1. The Y axis is the percent porosity. The results indicate the porosity of the cement as a function of the level of both the pore forming agent added and level of phosphoserine added.

EXAMPLE 7

The compositions of Table 7 were prepared and tested in the same manner as in Example 1. All testing was on cortical bovine bone. All testing was conducted at 5 minutes cure. All testing was 45° Shear/Tension.

TABLE 7

| Composition | 7A | 7B | 7C |
|---|---|---|---|
| TTCP | 400 mg | 400 mg | 400 mg |
| Phosphoserine | 185 mg | 185 mg | 185 mg |
| Water | 130 µl | 130 µl | 130 µl |
| β-TCP granules | 100 mg | 100 mg | 100 mg |
| Sodium Chloride | 10 mg | 25 mg | |
| Glycerol phosphate disodium | | | 25 mg |
| Adhesive Strength (kPa) | 2036 (n = 1) | 778 (n = 2) | 1931 (n = 1) |

EXAMPLE 8

The compositions of Table 8 were prepared and tested in the same manner as in Example 1. All testing was on cortical bovine bone. All testing was conducted at 5 minutes cure. All testing was 45° Shear/Tension unless otherwise indicated.

TABLE 8

| Composition | 8A | 8B | 8C | 8D |
|---|---|---|---|---|
| TTCP | 400 mg | 400 mg | 400 mg | 400 mg |
| Phosphoserine | 250 mg | 250 mg | 185 mg | 185 mg |
| Water | 130 µl | 130 µl | 130 µl | 130 µl |
| Serine | 33 mg | 16 mg | | |
| Mannitol | | | 25 mg | |
| Trehalose | | | | 60 mg |
| β-TCP granules | | | 100 mg | 100 mg |
| Adhesive Strength (kPa) | 160 (n = 1) (Shear); 610 (n = 1) @ 10 minute cure (Shear) | 750 (n = 1) (Shear); 1610 (n = 1) @ 10 minute cure (Shear) | 1603 (n = 1) | 386 (n = 1) |

EXAMPLE 9

The compositions of Table 9 were prepared and tested in the same manner as in Example 1. All testing was on cortical bovine bone unless otherwise indicated. All testing was conducted at 5 minutes cure unless otherwise indicated. All testing was 45° Shear/Tension unless otherwise indicated.

TABLE 9

| Composition | 9A | 9B | 9C |
|---|---|---|---|
| TTCP | 400 mg | 400 mg | 400 mg |
| Phosphoserine | 185 mg | 250 mg | 250 mg |
| Water | 140 µl | 175 µl | 175 µl |
| β-TCP granules | 100 mg | 133 mg | 133 mg |
| Calcium carbonate powder | | 14 mg | 14 mg |
| Calcium silicate | 100 mg | | |
| Silk, braided & ground | | 7 mg | |
| Bovine cortical bone powder | | | 53 mg |
| Adhesive Strength (kPa) | 2610 (n = 1); 350 (n = 1) cancellous | 5645 (n = 2) @ 10 min cure (3 pt bending) | 4360 (n = 2) @ 10 minute cure (3 Pt bending) |

EXAMPLE 10

The compositions of Table 10 were prepared and tested in the same manner as in Example 1. All testing was on cortical bovine bone unless otherwise indicated. All testing was conducted at 10 minutes cure unless otherwise indicated. All testing was 3 Pt bending unless otherwise indicated.

TABLE 10

| Composition | 10A | 10B | 10C |
|---|---|---|---|
| TTCP | 400 mg | 400 mg | 400 mg |
| Phosphoserine | 250 mg | 250 mg | 250 mg |
| Water | 175 µl | 175 µl | 135 µl |
| Calcium Carbonate | 14 mg | 14 mg | 14 mg |
| β-TCP granules | 133 mg | 133 mg | 133 mg |
| Collagen (Type 1) | 53 mg | | |
| PLGA (10:90) fiber | | 25 mg | |
| PLGA (50:50) fiber | | | 7 mg |
| Adhesive Strength (kPa) | 1925 (n = 2) | 4680 (n = 3) | 4730 (n = 2) |

EXAMPLE 11

The compositions of Table 11 were prepared and tested in the same manner as in Example 1. All testing was on cortical bovine bone unless otherwise indicated. All testing was conducted at 10 minutes cure unless otherwise indicated. All testing was 3 Pt bending unless otherwise indicated.

TABLE 11

| Composition | 11A | 11B | 11C |
|---|---|---|---|
| TTCP | 400 mg | 400 mg | 400 mg |
| Phosphoserine | 267 mg | 185 mg | 250 mg |
| Water | 160 µl | 130 µl | 175 µl |
| β-TCP granules | 100 mg | 100 mg | 133 mg |
| Calcium carbonate powder | | | 14 mg |
| PLGA (50:50) powder | 7 mg | | |
| PLLA-PEG-PLLA (5k:1k:5k) block copolymer | | 10 mg | |
| Keratin fiber (Human hair) | | | 7 mg |
| Adhesive Strength (kPa) | 2825 (n = 2) | 1819 (n = 1) @ 5 min cure (45° Shear/Tension) | 4950 (n = 2) |

EXAMPLE 12

The compositions of Table 12 were prepared and tested in the same manner as in Example 1. All testing was on cortical bovine bone unless otherwise indicated. All testing was conducted at 10 minutes cure unless otherwise indicated. All testing was 3 Pt bending unless otherwise indicated.

TABLE 12

| Composition | 12A | 12B | 12C |
|---|---|---|---|
| TTCP | 400 mg | 400 mg | 400 mg |
| Phosphoserine | 250 mg | 185 mg | 250 mg |
| Water | 175 µl | 160 µl | 130 µl |
| β-TCP granules | 133 mg | 100 mg | 133 mg |
| Calcium carbonate powder | 14 mg | | 14 mg |
| Osigraft (Collagen + BMP7) | 53 mg | | |
| BMP7 | | 250 µg | 200 µg |
| Lactose | | 7 mg | 5.6 mg |
| Adhesive Strength (kPa) | 2275 (n = 2) | 2530 (n = 2) | 6635 (n = 2) |

EXAMPLE 13

Formulations 2A and 5F were prepared and tested in the same manner as in Example 1 on both cortical and cancellous bone. Formulations 2A and 5F are similar except that composition 5F includes calcium carbonate. The cure time is shown in Tables 13A and 13B.

TABLE 13A

Cortical Bone

| | Cure Time | Composition 2A (n = 6) | Composition 5F (n = 6) |
|---|---|---|---|
| Tension | 2 min | 1.10 +/− 0.14 | 0.58 +/− 0.42 |
| | 5 min | 2.34 +/− 0.35 | 1.39 +/− 0.35 |
| Shear | 2 min | 1.63 +/− 0.30 | 1.33 +/− 0.20 |
| | 5 min | 2.69 +/− 0.30 | 1.83 +/− 0.33 |
| 3 Pt Bending | 2 min | 3.91 +/− 0.33 | 2.25 +/− 0.70 |
| | 5 min | 6.26 +/− 0.31 | 3.93 +/− 0.80 |
| | 24 hr | 7.79 +/− 1.20 | 4.47 +/− 0.39 |
| | 1 wk | 7.16 +/− 0.36 | 5.98 +/− 1.08 |

TABLE 13B

Cancellous Bone

| | Cure Time | Composition 2A (n = 6) | Composition 5F (n = 6) |
|---|---|---|---|
| Tension | 2 min | 0.25 +/− 0.05 | 0.24 +/− 0.05 (n = 4) |
| | 5 min | 0.45 +/− 0.11 | 0.41 +/− 0.08 (n = 4) |
| Shear | 2 min | 0.58 +/− 0.17 | 0.36 +/− 0.10 |
| | 5 min | 1.02 +/− 0.19 | 0.66 +/− 0.12 |
| 3 Pt Bending | 2 min | 0.72 +/− 0.06 | 0.32 +/− 0.23 |
| | 5 min | 0.86 +/− 0.11 | 0.66 +/− 0.28 |
| | 24 hr | 1.36 +/− 0.09 | 1.31 +/− 0.27 |
| | 1 wk | ND | ND |

ND = No Data

EXAMPLE 14

In order to see if the compositions can be used to fill a gap in bone, Formulations 1B and 1C were prepared and tested in the same manner as in Example 1. The bone cubes used for testing in Table 14 had apposing faces measuring 9×9.5 mm. The faces were cut at 90° angle. Prior to testing, the bone cubes were incubated within a phosphate buffered saline (PBS) solution bath at 30° C. To simulate a gap, 2 mm of composition was placed between one pair of bone while the no gap had a small amount, less than 0.25 mm thickness applied. The cure time is shown in Table 14. After the cure time indicated, the cubes were loaded onto the sample fixtures and tested on an Instron force test machine in the shear plane. A commercial product Mimix QS was prepared according to directions and tested as a control:

TABLE 14

| | Shear Strength (MPa) | |
|---|---|---|
| | 5 min Cure | 10 min Cure |
| Bovine Cortical Bones Adhesive Strength No Gap (<0.25 mm) Between Bones | | |
| Composition 1B (n = 6) | 3.30 +/− 0.15 | 3.20 +/− 0.57 |
| Composition 1C (n = 6) | 2.29 +/− 0.10 | 3.00 +/− 10.28 |
| Mimix QS (n = 6) Control | 0.09 +/− 0.8 | 0.99 +/− 0.20 |
| Bovine Cortical Bones Adhesive Strength 2 mm Gap Between Bones | | |
| Composition 1C applied at 1.5 min (n = 6) | 2.29 +/− 0.10 | 3.00 +/− 10.28 |
| Composition 1C applied at 2.5 min (n = 5) | 1.21 +/− 0.23 | 1.91 +/− 0.60 |
| Composition 1C applied at 3.5 min (n = 3) | 0.46 +/− 0.03 | 0.99 +/− 0.28 |

EXAMPLE 15

In order to see the effect of fibrous materials added as an intrinsic strength additive, a series of compositions set out in Table 15 were prepared and tested in the same manner as in Example 1. The bone cubes used for testing in Table 15 had apposing faces measuring 9×9.5 mm. The faces were cut at 90° angle. The cure time was 10 minutes. After the samples cured, the cubes were loaded onto the 3 pt bending sample fixture and tested on an Instron force test machine.

TABLE 15

| Composition | 3 Pt Bending Strength (MPa) @ 10 Min Cure |
|---|---|
| Composition 5G, No fiber (n = 2) | 0.75 |
| Composition 9B, silk fiber (n = 2) | 5.65 |
| Composition 10B, PLGA fiber (n = 2) | 4.68 |
| Composition 9C, cortical bone powder (n = 2) | 4.36 |
| Composition 11C, keratin hair fiber (n = 2) | 4.95 |

The addition of fibers as an additive has a positive effect on the bending strength of the samples tested compared to a sample with no fiber as an additive.

EXAMPLE 16

In order to test the effectiveness of the present compositions in binding bone to metals used in surgery such as screw augmentation, a sample of cancellous bone cube was drilled down the center with a drill having a diameter of 2.7 mm to a depth of 10 mm. The cancellous bone cube samples used for screw augmentation testing were from bovine source and had a density of 0.26+/−0.13 g/cm^2 based on PIXA densitometry scans. Each bone cube sample measured 10 mm×10 mm in cross section×2.5 cm in length. A stainless steel, cancellous bone screw with an outside thread diameter of 4 mm with 7 mm of thread length was engaged into the drilled hole. The threads were fully engaged into the bone; however, the shank or shaft of the screw between the threads and screw head was left exposed above the surface of the bone leaving a gripping space of 5 mm. The sample was clamped into a fixed vice located within an Instron load machine. A test fixture gripped under the head of the screw and the maximum force required to pull the screw from the bone at a rate=2 mm/min was measured. After the screw was pulled out, the stripped hole and surrounding cancellous bone pores were filled with 0.2-

Figure 2:
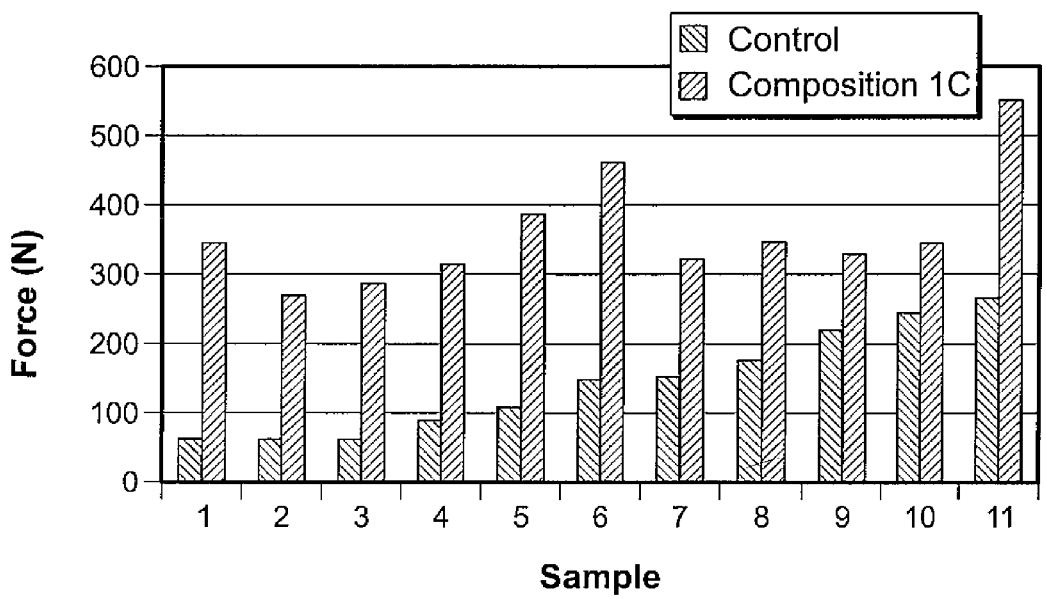
FIG. 2. is a graph comparing the screw pullout force for certain compositions against a control that did not use any added composition as described herein.

0.3 cc with Composition 1C using a 3 cc Terumo syringe and the screw was re-inserted into the stripped hole which was filled with the composition while it was in the working period. The composition was allowed to cure at 37° C. in a humidity chamber for 10 minutes. The screw pullout force was than re-tested demonstrating the screw augmentation properties of the composition. The results of the tests are shown in FIG. 2. The Y axis on the drawing is pullout force in Newton (N). The control screw pullout force was 143+/−76 N (n=11); and the screw pullout force augmented with Composition 1C was 360.0+/−82 N (n=11). This was on average a 213% increase in pullout strength compared to the control.

EXAMPLE 17

Figure 3:
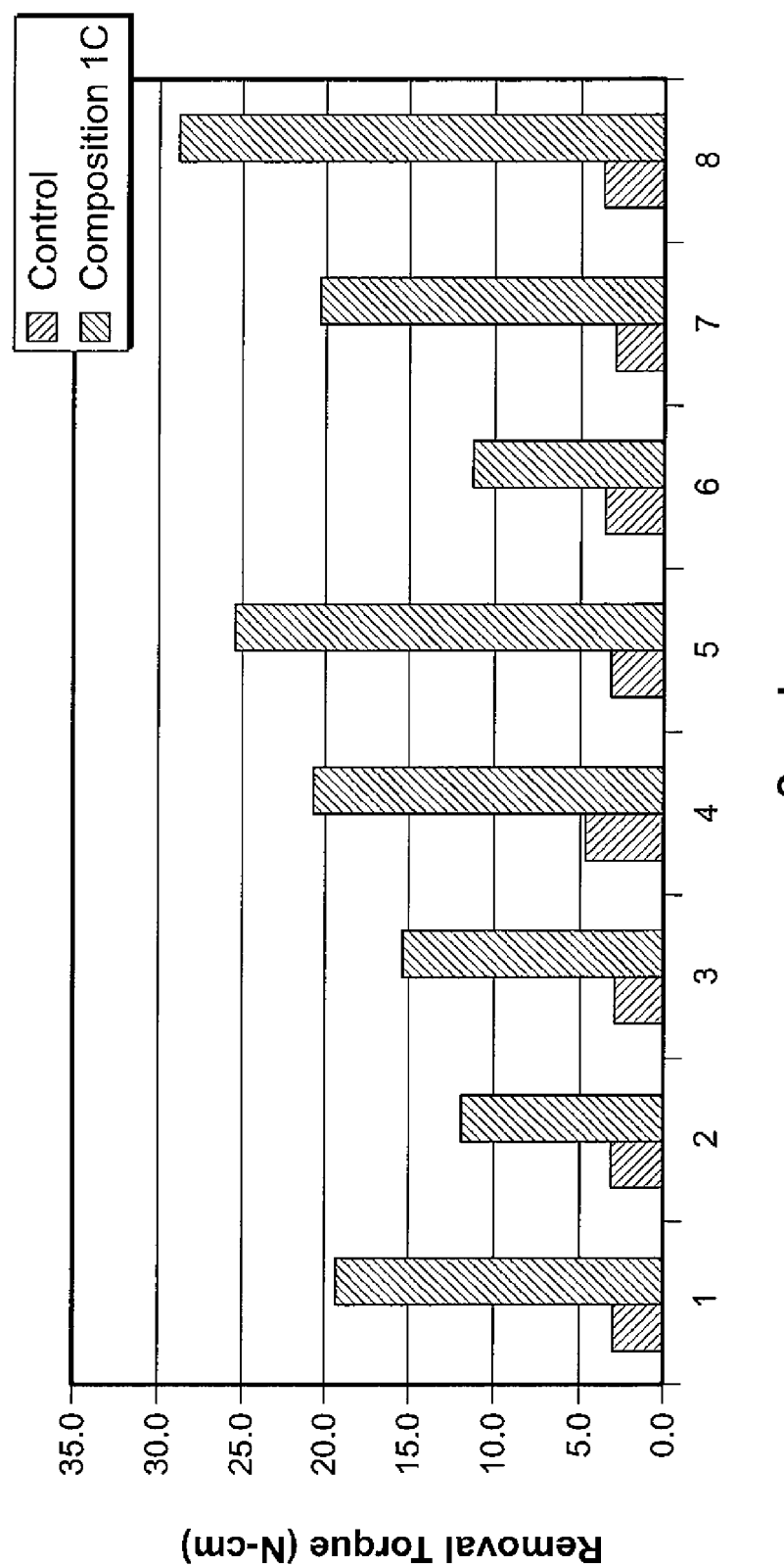
FIG. 3 is a graph comparing the screw removal torque for certain compositions against a control that did not use any added composition as described herein.

Example 16 was repeated except that the Instron testing was set up to test removal torque. Each bone cube sample was clamped into a fixed vice. A hand held torque gauge with appropriate tip was inserted into the head of the screw and the maximum torque required to remove the screw from the bone was measured. From the opposite end of the same cube (to mimic the same bone density), the sample was drilled down the center of the cube with a drill with a diameter of 2.7 mm and to a depth of 10 mm; however, this hole and the surrounding cancellous bone pores were filled with 0.2-0.3 cc of Composition 1C using a 3 cc Terumo syringe and the screw was inserted into the drilled hole which was filled with the composition while it was in the working period. The composition was allowed to cure at 37° C. in a humidity chamber for 10 minutes. The screw removal torque was measured demonstrating the screw augmentation properties of the composition. The results of the tests are shown in FIG. 3. The Y axis on the drawing is removal torque in Newton-centimeter (N-cm). The control screw removal torque was 4.7+/−0.8 N-cm (n=8); and the Composition 1C screw removal torque was 26.9+/−8.7 N-cm (n=8). This was on average a 480% increase in removal torque compared to the control.

EXAMPLE 18

The injectability into small bone void or onto bone surfaces using hand force was tested as follows. Composition 1C was mixed for 20-30 secs at 18-22° C. in an ambient environment using a spatula or pestle. After mixing, the composition was loaded into a 3 cc Terumo syringe and the composition was injected through the luer lock nozzle tip with a peak force not exceeding 150 N during the working period up through 3 min 30 sec from the start of mixing.

EXAMPLE 19

Composition tacky and bone re-apposition properties were evaluated throughout the working period. Prior to composition application, the bone cubes were incubated in a PBS solution bath held at 30° C. The bone cubes were removed from the bath for testing and the surfaces remained wet. The bone cubes were mounted into clamps (top and bottom) in vertical axis alignment within the Instron machine. A small gap of approximately 1 cm was between the top surface of the bottom cube and the bottom surface of the top cube. The Instron machine was located at room temperature conditions of 18-22° C. Immediately after mounting the bone cubes, Composition 1C was mixed per the instructions in Example 18. After mixing, the composition was applied to the top surface of the bottom bone cube using a spatula. After application, the Instron test program was run at 1 min from the start of mixing. The Instron program profile started by moving the top clamp down such that the bottom surface of the top bone cube came into contact with the upper surface of the bottom bone cube with a compression force of 5 N held for 10 seconds (apposition). The Instron then moved the top clamp in the vertical direction at 2 min/min to separate the bone cubes, thus measuring the separation strength of the composition (tacky property). This test was repeated at consecutive time periods throughout the tacky state (at 2 min and at 3.5 min from the start of mixing), demonstrating the re-apposition tacky property of the composition. The bone fragments exhibited tacky or separation strength, usually in the range of about 50-150 kPa of tension strength at these time points. Immediately after the bones were separated at 3.5 min, the bones were re-apposed and the composition was allowed to cure at room temperature for up to 6.5 min from the start of mixing and the final separation strength was measured which was typically greater then 1 MPa. This demonstrated that the composition allows the bone cubes to be reapposed several times throughout the tacky state, without compromising the final separation strength upon cure. This tacky and re-apposition property is present not only in tension, but also in the shear and bending planes.

EXAMPLE 20

Sufficient material cohesion in a wet surgical field was evaluated. Composition 1C was mixed per the instructions in Example 1. By 2 min from the start of mixing, the composition as a solid mass was submerged into water, PBS (pH was neutral 7.2-7.4), or blood at 37° C. After 24 hrs of incubation, the fluid containing any eluded particulate or soluble molecules from the composition was collected and visually negligible. In comparison to other commercially available calcium phosphate cements, such as HydroSet® Injectable HA Bone Substitute, the visual amount of particulate or soluble molecules in the composition elution was significantly less, demonstrating improved composition cohesiveness when subjected to a wet field environment.

EXAMPLE 21

Maintenance of bone fragment alignment to allow definitive hardware placement is critical in surgery. Composition 2A was mixed, applied to bones, and submerged to cure in a PBS bath at 30° C. as per the instructions in Example 1. By 2-10 minutes of cure time the adhesive separation strength increased to the range of 1-4.5 MPa in shear and tension strength, and in the range of 3-10 MPa in 3 pt bending strength. This strength would hold the fragments together intra-operatively to allow drilling of bone and placement of appropriate immobilization (definitive hardware fixation) such as plates and screws (metal or resorbable). This capacity eliminates or reduces the need to use K-wires or other temporary metal fixation devices, which can be difficult and awkward to use, as a temporary means to augment the bone fixation intra-operatively to allow appropriate immobilization.

EXAMPLE 22

Capacity to bind and prevent calcium based granule migration from the putty material was evaluated. Composition 2B, which contains β-TCP granules, was mixed per the instructions in Example 1 and could be molded during the working period into any desired shape for the intended defect. Further in vitro testing demonstrated these compositions while in the working period maintained consistency and prevented granule migration from the putty matrix when submerged in PBS held at 37° C. and maintained over a time period of at least 2 weeks. The β-TCP granules did not migrate from the putty; rather they were entrapped within the putty matrix.

EXAMPLE 23

Composition 2B exhibits tacky properties immediately after mixing which sticks to surgical gloves. When the intended use of the composition is a bone void filler to be applied manually by the surgeon's hands, this tacky property may be undesirable for surgeons. This tacky property to the gloves can be masked while maintaining the cohesive properties of the composition by adding PEG to the composition. Composition 2E containing PEG demonstrated this effect.

EXAMPLE 24

Compositions that exhibit exothermic properties while curing can be mitigated by adjusting variables as displayed by the compositions in Table 16. These compositions were mixed as described in Example 1 and then a thermocouple was placed into the middle of the composition while it was curing in each bowl. The temperature measurements were recorded over time. Compositions mixed as smaller volumes and using larger particle size TTCP had lower exothermic properties as did compositions that incorporated additives like sorbitol.

TABLE 16

Composition 1C was tested at various volumes of material (Small TTCP mean particle size used)

| Component | 1 cc | 3 cc | 5 cc |
|---|---|---|---|
| TTCP (Particle size Mean = 15-20 μm) | 1600 mg | 4800 mg | 8000 mg |
| Phosphoserine | 1000 mg | 3000 mg | 5000 mg |
| Water | 532 μl | 1595 μl | 2660 μl |
| Max Temperature during cure | 38.2° C. | 59.5° C. | 69.0° C. |

Composition 1C was tested at various volumes of material (Large TTCP mean particle size used)

| Component | 3 cc |
|---|---|
| TTCP (Particle size Mean = 25-35 μm) | 4800 mg |
| Phosphoserine | 3000 mg |
| Water | 1595 μl |
| Max Temperature during cure | 44.8° C. |

TABLE 16-continued

Composition 2A was tested at various volumes of material (Small TTCP mean particle size used)

| Component | 1 cc | 3 cc | 5 cc |
|---|---|---|---|
| TTCP (Particle size Mean = 15-20 μm) | 1600 mg | 4800 mg | 8000 mg |
| Phosphoserine | 740 mg | 2200 mg | 3700 mg |
| β-TCP granules | 400 mg | 1200 mg | 2000 mg |
| Water | 520 μl | 1595 μl | 2660 μl |
| Max Temperature during cure | 43.1° C. | 65.5° C. | 73.6° C. |

Composition 2A (with Sorbitol added) was tested at various volumes of material (Small TTCP mean particle size used)

| Component | 5 cc |
|---|---|
| TTCP (Particle size Mean = 15-20 μm) | 8000 mg |
| Phosphoserine | 3700 mg |
| β-TCP granules | 2000 mg |
| Sorbitol | 250 mg |
| Water | 2600 μl |
| Max Temperature during cure | 50.8° C. |

COMPARATIVE EXAMPLE 1

TTCP is a unique component of all the calcium based materials which interacts with the compounds that are structurally similar to phosphoserine to exhibit the range of useful properties described in this invention. Table 17 demonstrates this effect using the following calcium based powders in place of TTCP (Composition 1C): dicalcium phosphate dihydrate (DCPD), monocalcium phosphate monohydrate (MCPM), HA, β-TCP, octacalcium phosphate (OCP), & α-TCP. These compositions were mixed and applied to cortical bone cubes as described in Example 1. At 1.5 min from the start of mixing, the bone cubes were submerged in a PBS bath held at 30° C. In addition, a small amount of the composition (0.25 cc) was rolled into a ball and dropped into a vial containing 5 cc of PBS solution at 30° C. to observe the particulate washout during the cure. After mixing, compositions 17A through 17E all resulted in creamy compositions, but none had tacky properties which were highly evident with composition 1C (TTCP based). Further, these compositions had significant visual particulate washout and failed to adhere the bone cubes as they fell apart either immediately during placement or within 3 minutes of being submerged in the PBS bath. Composition 17F has some appreciable tacky properties; however, there was visual particulate washout observed in the PBS solution and moreover the adhesive strength was inferior in comparison to 1C.

TABLE 17

| Composition | 1C | 17A | 17B | 17C | 17D | 17E | 17F |
|---|---|---|---|---|---|---|---|
| TTCP | 400 mg | | | | | | |
| DCPD | | 400 mg | | | | | |
| MCPM | | | 400 mg | | | | |
| β-TCP | | | | 400 mg | | | |
| HA | | | | | 400 mg | | |
| OCP | | | | | | 400 mg | |
| α-TCP | | | | | | | 400 mg |
| Phosphoserine | 250 mg | 250 mg | 250 mg | 250 mg | 250 mg | 250 mg | 250 mg |
| Water | 130 μl | 130 μl | 130 μl | 130 μl | 130 μl | 465 μl | 130 μl |
| Tacky properties | A | C | C | C | C | C | B |

TABLE 17-continued

| Composition | 1C | 17A | 17B | 17C | 17D | 17E | 17F |
|---|---|---|---|---|---|---|---|
| Wet field cohesion in putty state | D | F | F | F | F | F | E |
| Adhesive strength, kPa | 2290 (n = 3) (Shear) | 0 | 0 | 0 | 0 | 0 | 250 (n = 3) (Shear) |

[A]Composition has sticky properties to bone, metal surfaces, and surgical gloves
[B]Composition has some sticky properties to bone, metal surfaces, and surgical gloves
[C]Composition has creamy properties, but does not stick to bone, metal, or surgical gloves
[D]Putty remained intact as a solid mass, no visual particulate washout
[E]Putty disintegrated partially, moderate visual particulate washout
[F]Putty disintegrated completely, significant visual particulate washout These compositions as disclosed in this specification can be used for a variety of medical applications. These include the capacity to allow or enhance fracture fixation by adhering both load and non-load bone fragments together alone or in the presence of appropriate immobilization (definitive hardware fixation); capacity to adhere middle ear ossicles and prosthesis together for ossicular chain reconstruction; capacity to enhance screw or bone anchor fixation in low density cancellous bone at and/or after surgery; capacity to allow screw fixation when the core diameter of the screw hole in bone is larger then the screw major diameter; capacity to provide bony contour and/or facial bone augmentation properties; capacity to adhere a metal or bioresorbable plate to fractured bones allowing for reduction and/or elimination of metal or bioresorbable screws used to fix plate to bone; capacity to enhance fixation of a joint replacement prosthesis to bone (e.g. hip acetabular cup or femoral stem), capacity to adhere the junction of at least one of a tendon, ligament, cartilage, a bone graft, and/or a dental implants to bone; capacity to adhere to bony defect perimeters while filling gaps creating a seal to prevent leakage (e.g. cerebral spinal fluid), and capacity to support new bone growth for dental socket or dental ridge augmentation. The compositions may be useful in human use applications and are also useful in veterinary applications. Lastly, the compositions may be useful in similar non-medical applications (e.g. carpentry, construction, under water use) as the compositions will adhere to a wide variety of surfaces including wood, glass, certain plastics, plaster, metals of all types, ceramic materials and the like.

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A method of repairing a hard surface comprising the steps of:
mixing a composition comprising an effective amount of tetra calcium phosphate and a compound of the formula

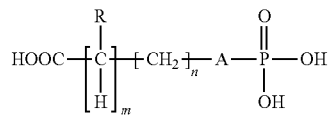

where A is O, $CH_2$, or S; R is H, $NH_2$, $NHCO(CH_2)_t CH_3$ where t is 0 to 2, $NH(CH_2)_x CH_3$ where x is 0 to 3, $NR1R2$ where R1 is $(CH_2)_y CH_3$ and R2 is $(CH_2)_y CH_3$ where y is 0 to 2, $(CH_2)_z CH_3$ where z is 0 to 3, where m is 0 to 1, and where n is 0 to 3 and wherein the compound is present in an amount from about 10% to about 90% by weight based on the combined weight of the tetra calcium phosphate and the compound,
with sufficient aqueous medium to create a mixture;
applying the mixture to the hard surface to be repaired; and
allowing the mixture to cure.

2. The method of claim 1 wherein the hard surface is bone.

3. The method of claim 2 wherein the mixture is applied to a void in the bone to fill the void.

4. The method of claim 1 wherein the compound is present in an amount from about 15% to about 50% by weight based on the combined weight of the of the tetra calcium phosphate and the compound.

5. The method of claim 1 wherein the compound is present in an amount of about 20% to about 40% by weight based on the combined weight of the of the tetra calcium phosphate and the compound.

6. The method of claim 1 wherein the compound is selected from the group consisting of phosphoserine, carboxy ethyl phosphonate, phoshonoacetic acid, and mixtures thereof.

7. The method of claim 1 wherein R is H, or $NH_2$.

8. The method of claim 1 wherein the compound is phosphoserine.

9. The method of claim 1 wherein the composition has a mean particle size of less than 1000 microns.

10. The method of claim 1 wherein the aqueous medium is a blood based product.

11. The method of claim 1 wherein the aqueous medium is water.

12. The method of claim 1 wherein the composition further includes an additive.

13. The method of claim 1 wherein the mixture has a tacky state for up to 12 minutes after mixing with the aqueous medium.

14. The method of claim 13 wherein the mixture during the tacky state has a separation strength in the range of about 10 kPa to about 250 kPa after mixing with the aqueous medium.

15. The method of claim 1 wherein the mixture composition has a putty state for up to 15 minutes after mixing with the aqueous medium.

16. A method of repairing bone structure comprising the steps of:
applying a composition comprising an effective amount of tetra calcium phosphate and a compound of the formula

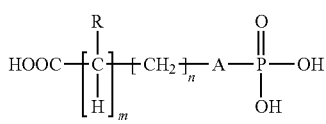

where A is O, $CH_2$, or S; R is H, $NH_2$, $NHCO(CH_2)_tCH_3$ where t is 0 to 2, $NH(CH_2)_xCH_3$ where x is 0 to 3, NR1R2 where R1 is $(CH_2)_yCH_3$ and R2 is $(CH_2)_yCH_3$ where y is 0 to 2, $(CH_2)_zCH_3$ where z is 0 to 3, where m is 0 to 1, and where n is 0 to 3 and wherein the compound is present in an amount from about 10% to about 90% by weight based on the combined weight of the tetra calcium phosphate and the compound directly to the bone structure to be repaired; and allowing the composition to harden by combining in situ with aqueous based bodily fluids.

17. The method of claim 16 wherein the compound is present in an amount from about 15% to about 50% by weight based on the weight of the of the tetra calcium phosphate and the compound.

18. The method of claim 16 wherein the compound is present in an amount of about 20% to about 40% by weight based on the combined weight of the of the tetra calcium phosphate and the compound.

19. The method of claim 16 wherein the compound is selected from the group consisting of phosphoserine, carboxy ethyl phosphonate, phoshonoacetic acid, and mixtures thereof.

20. The method of claim 16 wherein R is H, or $NH_2$.

21. The method of claim 16 wherein the compound is phosphoserine.

22. The method of claim 16 wherein the composition has a mean particle size of less than 1000 microns.

23. The method of claim 16 wherein the composition further includes an additive.

24. A method of joining bone to another material comprising the steps of:

mixing a composition comprising an effective amount of tetra calcium phosphate and a compound of the formula

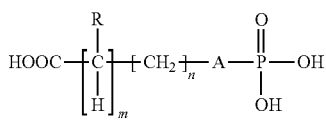

where A is O, $CH_2$, or S; R is H, $NH_2$, $NHCO(CH_2)_tCH_3$ where t is 0 to 2, $NH(CH_2)_xCH_3$ where x is 0 to 3, NR1R2 where R1 is $(CH_2)_yCH_3$ and R2 is $(CH_2)_yCH_3$ where y is 0 to 2, $(CH_2)_zCH_3$ where z is 0 to 3, where m is 0 to 1, and where n is 0 to 3 and wherein the compound is present in an amount from about 10% to about 90% by weight based on the combined weight of the tetra calcium phosphate and the compound, with sufficient aqueous medium to create a mixture;

applying the mixture to a surface of the bone;

placing the surface of the bone into contact with a material to be joined to the bone; and allowing the mixture to cure.

25. The method of claim 24 wherein the other material is a soft tissue.

26. The method of claim 24 wherein the other material is a metal.

27. The method of claim 24 wherein the other material is a ceramic.

28. The method of claim 24 wherein the other material is a bioglass.

29. The method of claim 24 wherein the other material is bone.

30. The method of claim 24 wherein the mixture is allowed to cure without the application of external pressure.

31. The method of claim 1 wherein the mixture has a tacky state for up to 4 minutes after mixing with the aqueous medium.

32. The method of claim 1 wherein the mixture has a tacky state for up to 2 minutes after mixing with the aqueous medium.

33. The method of claim 1 wherein the mixture composition has a putty state for up to 8 minutes after mixing with the aqueous medium.

34. The method of claim 1 wherein the mixture composition has a putty state for up to 5 minutes after mixing with the aqueous medium.

35. The method of claim 13 wherein the mixture during the tacky state has a separation strength in the range of about 50 kPa to about 150 kPa after mixing with the aqueous medium.

* * * * *